United States Patent [19]

Welstead, Jr. et al.

[11] 4,151,282

[45] Apr. 24, 1979

[54] COMPOSITIONS AND METHODS FOR TREATING DIABETIC COMPLICATIONS

[75] Inventors: William J. Welstead, Jr.; Warren N. Dannenburg, both of Richmond, Va.

[73] Assignee: A. H. Robins Company, Inc., Richmond, Va.

[21] Appl. No.: 865,756

[22] Filed: Dec. 29, 1977

[51] Int. Cl.² ............................................. A61K 31/47
[52] U.S. Cl. ................................................... 424/258
[58] Field of Search ................................ 424/262, 258

[56] References Cited

U.S. PATENT DOCUMENTS 3,821,383  6/1974  Sestanj et al. ........................ 424/258

OTHER PUBLICATIONS

Science, 182, 1146 (1973).

Primary Examiner—Frederick E. Waddell

[57] ABSTRACT

Methods for using 5,6-dihydro-4H-pyrrolo[3,2,1-ij]quinoline-1,2-dione and pharmaceutical compositions thereof in preventing diabetic complications are disclosed.

3 Claims, No Drawings

COMPOSITIONS AND METHODS FOR TREATING DIABETIC COMPLICATIONS

BACKGROUND OF THE INVENTION

1. Field of the Invention

The present invention is concerned with methods for preventing and treating complications associated with diabetes mellitus. More specifically, the methods of the present invention are useful for the prevention and treatment of various diabetic complications including cataracts, neuropathy, retinopathy and nephropathy.

2. Description of the Prior Art

It has been established that high levels of polyols such as sorbitol and galactitol accumulate in certain tissues of the human body as, for example, ingalactosemia and certain diabetic complications. The polyols are formed in the body by the enzymatic reduction of various hexoses such as glucose and galactose by the enzyme aldose reductase. In particular, the accumulation of the polyols in the lens and retina tissue of diabetic persons is responsible for the formation of cataracts and the concomitant loss of lens clarity. The investigations of Kenneth H. Gabby, New England Journal of Medicine 288 (16), 831–836 (1973) and refernces cited therein, and J. H. Kinoshita et al, Biochem. Biophys. Acta., 158, 472 (1968) and references cited therein have shown that inhibitors of aldose reductase effectively delay cataract formation in rats fed galactose. Thus, an agent which inhibits aldose reductase affords a potential means of preventing cataract formation in persons afflicted with diabetes and galactosemia. U.S. Pat. No. 3,821,383 discloses certain benzoquinoline acetic acids as useful in preventing or relieving diabetic complications. Science, 182, 1146 (1973) discloses 1,3-dioxo-1H-benz-[de]isoquinoline-2(3H) acetic acid (AY-22,284) as an aldose reductase inhibitor which effectively suppressed the formation of cataracts in galactosemic rats.

SUMMARY OF THE INVENTION

According to the present invention there is provided 5,6-dihydro-4H-pyrrolo[3,2,1-ij]quinoline-1,2-dione of the formula:

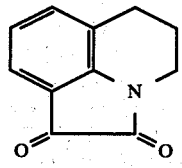

Formula I pharmaceutical compositions thereof and methods for the use of said pharmaceutical compositions in diabetic mammals for the prophylaxis and treatment of diabetic complications.

It is therefore an object of the present invention to provide 4,5-dihydro-4H-pyrrolo[3,2,1-ij]quinoline-1,2-dione and a method for its preparation. Another object is to provide compositions containing 4,5-dihydro-4H-pyrrolo[3,2,1-ij]quinoline-1,2-dione and a pharmaceutical carrier. A still further object is to provide a method for the use of compositions containing 4,5-dihydro-4H-pyrrolo[3,2,1-ij]quinoline-1,2-dione for the prophylaxis and treatment of diabetic complications. These and other objects will become apparent from the description which follows.

DETAILS OF THE INVENTION

As discussed hereinabove, sugar cataract formation is a frequent complication of the diabetic patient and their occurrence is apparent even in patients where diabetes appears controlled. The involvement of the enzyme aldose reductase in the formation of sugar cataracts has been demonstrated as shown in the discussion of the prior art, said aldose reductase catalyzing the production of sorbitol from glucose and galactitol (dulcitol) from galactose. The accumulation of polyols in the lens tissue results in osmotic and histological changes which are characteristic of sugar cataracts. More specifically, galactose has been shown to be a cataractogenic agent and the inhibition of cataract formation in galactose fed rats provides a means for evaluating the efficacy of a chemical entity for the prophylaxis and treatment of polyol-induced cataracts.

Male albino rats of the Spraque-Dawley strain weighing 300–450 g. were used to evaluate the efficacy of 5,6-dihydro-4H-pyrrolo[3,2,1-ij]quinolin-1,2-dione as an aldose reductase inhibitor. The compound was compared against the known orally active inhibitor of aldose reductase, 1,3-dioxo-1H-benz[de]isoquinoline-2(3H)acetic acid (AY-22,284). Control rats received a 10% galactose solution at a dose level of 10 ml/kg. daily for three days. The total dose was 1 g/kg daily. Six animals per control group were used. Groups receiving galactose plus test drug contained three rats. The routine starting dose of a test drug was 100 mg/kg. orally for three days with galactose given simultaneously. The test drug was administered at a volume of 5 ml/kg. The test drug solution and the galactose solution were administered together. Twenty-four hours after the third dose the lens of the eyeballs were carefully removed from the sacrificed rats and the polyol content of the lens determined according to West and Rapport, Proc. Soc. Exp. Biol. Med. 70, 141–142 (1949). The data are given in Table 1.

Table 1

| Compound | Dose mg/kg PO | No. of Rats | Micromoles Dulcitol/g of Tissue | %± Control |
|---|---|---|---|---|
| Experiment No. 1 | | | | |
| Galactose Controls | — | 6 | 3.7 | — |
| Ay-22,284[1] | 200 | 3 | 2.7 | −27 |
| AHR-5191[2] | 100 | 3 | 2.1 | −43.2 |
| Experiment No. 2 | | | | |
| Galactose Controls | — | 6 | 4.3 | — |
| Ay-22,284 | 100 | 3 | 5.9 | +37.2 |
| AHR-5191 | 100 | 3 | 2.7 | −37.0 |

[1]AY-22,234 is 1,3-dioxo-1H-benz[de]isoquinoline-2(3H)acetic acid
[2]AHR-5191 is 5,6-dihydro-4H-pyrrolor[3,2,1-ij]quinoline-1,2-dione The ability of 4,5-dihydro-4H-pyrrolo[3,2,1-ij]quinoline-1,2-dione to inhibit aldose reductase activity was determined according to the procedure of Lineweaver, H., and Burk D., The Determination of Enzyme Dissociation Constants, J. Am. Chem. Soc. 658–666 (1934).

Aldose reductase was isolated from bovine lens and the activity of the enzyme determined according to Gabbay, R. H. and Kinoshita, J. H., Methods in Enzymology, Vol. XLI (B) 37:159.

The amount of 4,5-dihydro-4H-pyrrolo[3,2,1-ij]quinoline-1,2-dione which inhibits the maximum velocity of the aldose reductase activity by 50% ($IC_{50}$) is 0.08 mM. determined by the procedure of Lineweaver and Burk loc cit. The IC$_{50}$ of 1,3-dioxo-1H-benz-[de]isoquinoline-2(3H)acetic acid is 0.09 mM.

EXAMPLE 1

5,6-Dihydro-4H-pyrrolo[3,2,1-i]quinoline-1,2-dione.

A solution of 133 g. (1 mole) of 1,2,3,4-tetrahydroquinoline in 750 ml. of dry ether was added dropwise over 30 minutes to 170 ml. of oxalyl chloride in 500 ml. of dry ether. The mixture was refluxed for four hours and concentrated under vacuum to a semi-solid. The mixture was treated with 300 ml. chloroform and concentrated again. As the last bit of solvent was removed, the mixture warmed spontaneously and cyclization of the 1,2,3,4-tetrahydroquinoline-1-oxalyl chloride took place. The resulting red solid was triturated with hot methanol and filtered (67 g.). The filtrate was concentrated, dissolved in benzene and passed through a short column of magnesium silicate. The effluent was concentrated and triturated with methanol. The resulting solid (18 g.) was combined with the product previously obtained. The total yield was 85 g. (45%). The recrystallized product (methanol) melted at 195°–197° C.

Analysis: Calculated for $C_{11}H_9NO_2$: C,70.58; H,4.85; N,7.48.

Found: C,70.81; H,4.92; N,7.48.

The invention further provides pharmaceutical compositions comprising, as active ingredient, the compound according to the invention in association with a pharmaceutical carrier or excipient. The compound may be presented in a form suitable for oral or parenteral administration. Thus, for example, compositions for oral administration are a solid or liquid and can take the form of capsules, tablets, coated tablets, suspensions, etc., employing such carriers or excipients conveniently used in the pharmaceutical art. Suitable tableting excipients include lactose, potato and maize starches, talc, gelatin and stearic and silicic acids, magnesium stearate and poyvinyl pyrrolidone.

For parenteral administration, the carrier or excipient can be a sterile, parenterally acceptable liquid, e.g., water, or a parenterally acceptable oil, e.g., arachis oil, contained in ampoules.

Advantageously, the compositions are formulated as dosage units, each unit being adapted to supply a fixed effective dose of active ingredient. Unit dosages are usually from 5 milligrams or above and preferably 25, 50 or 100 milligrams. Obviously, several unit dosage forms may be administered at about the same time.

The following are examples formed in accordance with this invention:

(1) Capsules

Capsules of 5 mg., 25 mg., 50.0 mg. and 100.0 mg. of active ingredient per capsule are prepared.

| Typical blend of encapsulation | mg. per capsule |
| --- | --- |
| Active ingredient | 5.0 |
| Lactose | 140.0 |
| Starch | 40.0 |
| Total | 185.0 |

Uniformly blend the active ingredient with lactose and starch and encapsulate the blend.

Additional capsule formulations contain a higher dose of active ingredient and are as follows:

| Ingredients | 25 mg. per Capsule | 50 mg. per Capsule | 100 mg. per Capsule |
| --- | --- | --- | --- |
| Active ingredient | 25.0 | 50.0 | 100.0 |
| Lactose | 300.0 | 271.7 | 231.5 |
| Starch | 110.0 | 113.0 | 103.5 |
| Total | 435.0 | 435.0 | 435.0 |

(2) Tablets

A typical formulation for a tablet containing 5.0 mg. of active ingredient per tablet follows. The formulation may be used for other strenfgths of active ingredient by adjustment of weight of dicalcium phosphate.

|  | Per tablet, mg. |
| --- | --- |
| (1) Active ingredient | 5.0 |
| (2) Corn starch | 13.6 |
| (3) Corn starch (paste) | 3.4 |
| (4) Lactose | 79.2 |
| (5) Dicalcium phosphate | 68.0 |
| (6) Calcium stearate | 0.9 |
| Total | 170.1 |

Uniformly blend 1, 2, 4 and 5. Prepare 3 as 10 percent paste in water. Granulate the blend with starch paste and press the wet mass through an eight mesh screen. The wet granulation is dried and sized through a twelve mesh screen. The dried granules are blended with the calcium stearate and compressed.

Additional tablet formulations contain 25.0 mg., 50.0 mg. and 100.0 mg. of active ingredient per tablet. The tablets are prepared according to the foregoing formulation by adjustment of weight of dicalcium phosphate.

INTRAMUSCULAR INJECTION

Ingredients

| 1. Active ingredient | mg. 5.0 |
| --- | --- |
| 2. Isotonic buffer solution 4.0, | q.s. to ml. 2.0 |

Procedure:

(1) Dissolve the active ingredient in the buffer solution.

(2) Aseptically filter the solution from step No. 1.

(3) The sterile solution is now aseptically filled into sterile ampoules.

(4) The ampoules are sealed under aseptic conditions.

Various modifications and equivalents will be apparent to one skilled in the art and may be made in compositions, methods and procedures of the present invention without departing from the spirit or scope thereof, and it is therefore to be understood that the invention is to be limited only by the scope of the appended claims.

We claim:

1. A method for the prevention or amelioration of diabetes complications consisting of cataracts in a diabetic animal which comprises orally administering to said animal an efffective amount of 5,6-dihydro-4H-pyrrolo[3,2,1-ij]quinoline-1,2-dione.

2. The method of claim 1 wherein the effective amount is from 5 milligrams to 100 milligrams.

3. A pharmaceutical composition for the prevention or amelioration of diabetes complications consisting of cataracts in a diabetic animal comprising (a) from 5 milligrams to 100 milligrams of 5,6-dihydro-4H-pyrrolo[3,2,1-ij] quinoline-1,2-dione and (b) a pharmaceutically acceptable carrier.

* * * * *